United States Patent [19]
Kim et al.

[11] Patent Number: 6,100,685
[45] Date of Patent: Aug. 8, 2000

[54] HIGH FREQUENCY MEASURING SYSTEM FOR MAGNETIC PROPERTIES OF MATERIALS

[75] Inventors: Ki Uk Kim; Jae Sung Song, both of Kyongsangnam Do, Rep. of Korea

[73] Assignee: Korea Electrotechnology Research Institute, Kyongsangnam Do, Rep. of Korea

[21] Appl. No.: 09/026,501

[22] Filed: Feb. 19, 1998

[30] Foreign Application Priority Data

Feb. 20, 1997 [KP] DPR of Korea ............ 1997-5170

[51] Int. Cl.[7] ................. G01R 33/12; G01R 33/14; G01N 27/72
[52] U.S. Cl. ................. 324/223; 324/211; 324/222; 324/225; 324/239
[58] Field of Search ............... 324/210–212, 324/222, 223, 225, 239–243

[56] References Cited

U.S. PATENT DOCUMENTS

| | | |
|---|---|---|
| 4,532,802 | 8/1985 | Yeack-Scranton et al. ...... 324/212 X |
| 5,241,269 | 8/1993 | Kamiya et al. .............. 324/223 |
| 5,394,083 | 2/1995 | Jiles ...................... 324/223 |
| 5,517,106 | 5/1996 | Longini .................... 324/142 |
| 5,532,590 | 7/1996 | Yamanaka .................. 324/223 X |
| 5,537,036 | 7/1996 | Sato et al. ................ 324/239 |

OTHER PUBLICATIONS

Manly, Jr., A 5.5–KOe 60–HZ Magnetic Hysteresis Loop Tracer with Precise Digital Readout, IEEE Trans. on Mag. pp 442–446, Sep. 1971.

Thottuvelil et al; High–Frequency Techniques For Magnetic Cores IEEE Power Electronics Specialists Conference 1985 pp 412–425, (no mo.).

Sato et al; 100KHz–10MHz Iron Loss Measuring System IEEE Transactions on Magnetics vol. MAG–23, No. 5, pp. 2593–2595, Sep. 1987.

*Primary Examiner*—Gerard Strecker
*Attorney, Agent, or Firm*—Flynn, Thiel, Boutell & Tanis, P.C.

[57] ABSTRACT

A high frequency magnetic properties measuring system is used for measurement of high frequency magnetic properties, for example high frequency core-loss and magnetic hysteresis curve (coercivity force, magnetic flux density, permeability) in soft magnetic materials such as ferrites, permalloy and amorphous magnetic cores used in inductors, transformers and filters of various electric and electromagnetic systems and devices such as computers and multimedia devices. A digital oscilloscope is operated as a waveform detection unit for measuring magnetic fields and magnetic flux density. A signal generator and a power amplifier are operated as a signal input unit. The digital oscilloscope and the signal generator are remotely controlled through a General Purpose Interface Bus by the computer. The high frequency magnetic properties are measured by remote control and the resulting data can be outputted and stored by the computer. When measuring the high frequency signal, the core-loss can be analyzed by applying suitable waveforms.

6 Claims, 7 Drawing Sheets

B-H curve varied with operating flux densities (0.1T, 0.2T, 0.3T, 0.4T)

The difference of shape between sine wave excitation and square wave excitation.

B-H curve of ferrite ring core at frequency 1 MHz.

HIGH FREQUENCY MEASURING SYSTEM FOR MAGNETIC PROPERTIES OF MATERIALS

FIELD OF THE INVENTION

This invention relates to a system for measuring magnetic properties in high frequency. More particularly, the invention relates to a system for high frequency measuring of magnetic properties, such as the core-loss and the magnetic hysteresis curve (coercivity, magnetic flux density, permeability) of a ferrite or a permalloy for an inductor, a transformer, a filter, and an amorphous magnetic core of the soft magnetic materials, which are used in computers, multimedia applications as well as other various electric and electronic devices.

BACKGROUND OF THE INVENTION

As is widely known, there are analog and digital methods for high frequency measuring of magnetic properties. In the analog method, it is not possible to store and process the measured data in a digital computer since the data, of magnetic properties, which is displayed as voltage by the general purpose oscilloscope, can only be read. However in case of high frequency measurement, the data measured has to be recorded within a short period because rapid heat emission of a sample leads to measurement errors. Therefore, in the analog method, the high frequency measurement of the above materials over a few KHz frequency is really difficult due to an impossibility of storing and controlling the data through a computer.

For the above reasons, the high frequency measurement of the magnetic properties such as a core-loss and a hysteresis curve of the materials mentioned is almost always performed by the digital method.

The conventional digital method mainly consists of the following measurements:

- measuring the magnetic properties of the materials by mounting the interface card of A/D converter and high speed data bus respectively to a computer;
- measuring the magnetic properties using an oscilloscope;
- recording a waveform by using an exclusive digitizer;
- measuring only core-loss by allowing the power-meter to have digital function; and
- measuring the core-loss by using the high speed A/D converter circuit and the signal generator.

Both of the measuring methods of (1) mounting the interface card of the A/D converter and high speed data bus to a computer and (2) recording a waveform by using the exclusive digitizer have substantially a high horizontal resolution, but they have difficulty when measuring in a high frequency over the MHz range, as well as a disadvantage due to the higher expense of a system.

Also the digitized power-meter has a disadvantage, wherein it cannot measure the waveform of a magnetic hysteresis curve, even though it is able to measure a core-loss up to the range of several hundred KHz range by using the A/D converter to digitize the received signal.

The method utilizing a digital oscilloscope obtains a magnetic hysteresis curve by initially recording the received waveform in the digital oscilloscope and subsequently processing it in a computer. The method using the single measuring group containing a high speed A/D converter circuit and a signal generating circuit obtains only necessary select functions among the combined functions between an oscilloscope and a computer. Therefore in the measurement of a core-loss and a magnetic hysteresis curve over MHz frequency range, both of these methods are substantially adopted.

SUMMARY OF THE INVENTION

It is therefore an object of the present invention to solve the above problems by providing a system for high frequency measuring of the magnetic properties, which system can accurately measure the phenomena of a magnetization curve (B-H) being produced by automatically adjusting the measuring period (waveform cycle). A computer controls the digital oscilloscope and the signal generator. The existing signal generator, a digital oscilloscope and a power amplifier, etc. can be used independently of the system for other general conventional purposes. Also, a computer can read and process the waveforms of the object samples to measure the required frequency, the core-loss and the magnetic values of the operating magnetic flux, as well as the magnetic hysteresis curve according to the conditions of the shapes and so forth of the samples. Thus, the present invention solves the disadvantages of the conventional measuring system attempting to measure in high frequency. The solved disadvantages include measuring frequency limitations, impossibility of storing and processing of data, impossibility of recording a high-frequency waveform within a short period through automatic input-output measurement for preventing heat-generation. In addition to the above, the magnetic core-loss in a practical application can be evaluated for the purpose of having the various magnetic waveforms such as a square waveform applied practically in the inventive high-frequency measuring equipment.

The above and other objectives, features and advantages of the invention will become more apparent from the following description when taken in conjunction with the accompanying drawings.

DETAILED DESCRIPTION OF THE PREFERRED EMBODIMENT

High frequency recording of a waveform is accomplished by recording the output waveform under the required measuring condition and subsequently interrupting the input signal to decrease heat-generation due to eddy current loss and to minimize the error resulting from heat-generation.

Therefore, a greater importance should be given to high frequency measuring techniques for the field, so that the problem can be solved with a full automation of the measuring as the frequency becomes higher by interconnecting the input data to a computer. Also, a computer is indispensable for processing the measured data regardless of how well the measuring equipment is automatized.

Of course, even in the conventional high frequency measurement a computer has been used. However, a system is not fully automatized except for only a partial automation such as an output portion. So the method is ineffective from the point of work-performance due to processing the data by inputting them again into a computer.

Figure 1:
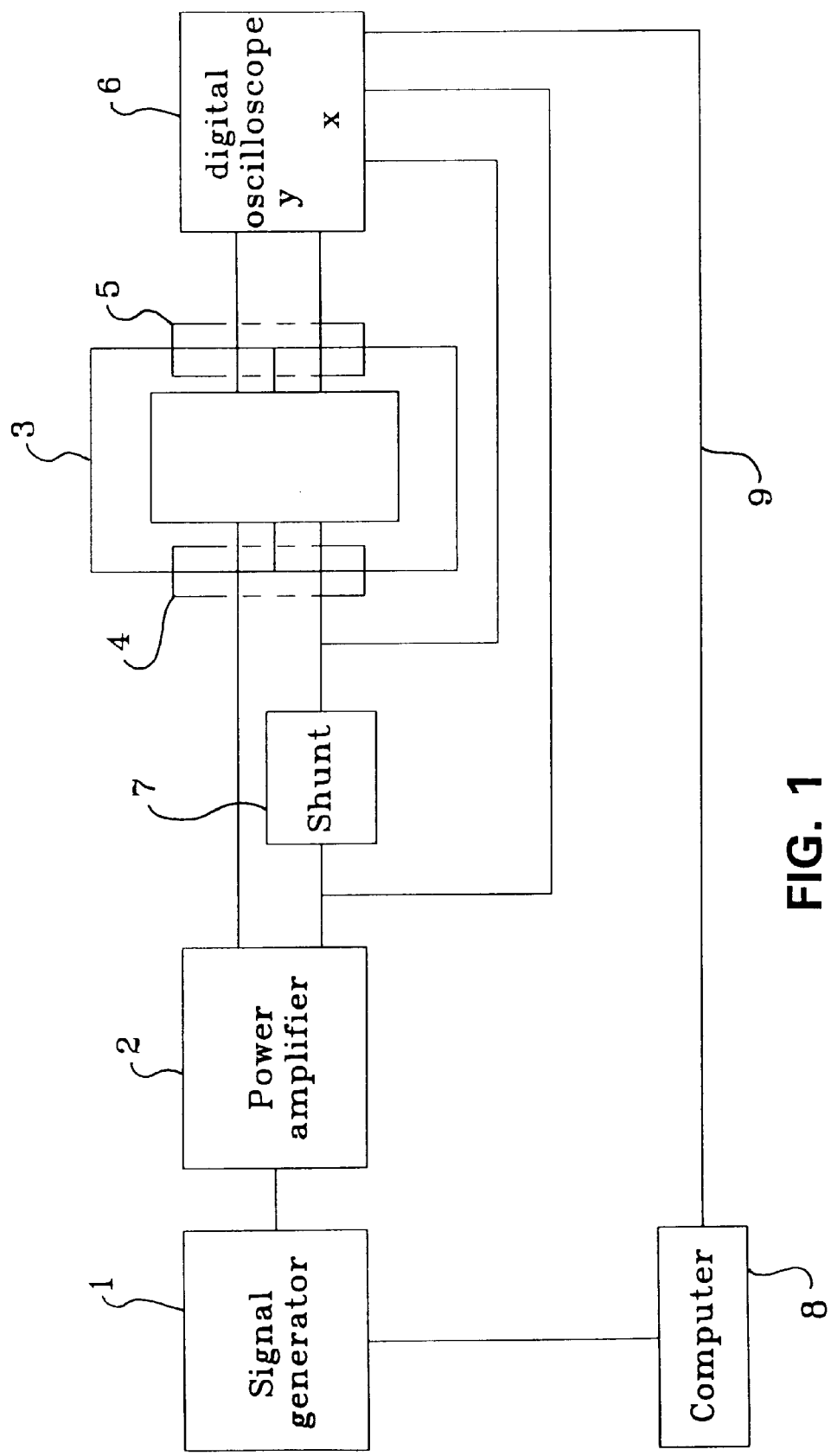
FIG. 1 is a block diagram showing a system of the present invention.

FIG. 1 is a block diagram showing a whole system of the present invention, a system including: a signal generator 1 for outputting a select waveform; a power amplifier 2 for amplifying the waveform outputted from the signal generator; a shunt 7 for converting current applied to the first coil 4 into a high frequency voltage, and outputting the waveform of that waveform and a digital oscilloscope 6 for measuring the frequency and the maximum value of the high-frequency voltage waveform of high frequency voltage waveform channels, which measured valued are sampled into a digital form and then stored in the memory of the oscilloscope as well as analyzed therein. One of the waveforms received via the first channel is magnetic field intensity (H) converted from the shunt 7, and the other waveform received via the second channel is magnetic flux density (B) of a sampler material 3. The system also has a computer 8 which controls the whole system, such as finally deciding an output of the signal generator 1 by feeding back the signal generator output as the measured values of the digital oscilloscope 6, storing the voltage waveform equivalent to each H and B magnetic field generated by the set signal from the generator 1 in the digital oscilloscope 6, and calculating a value of H and B waveform and high-frequency hysteresis curve. A computer can calculate various magnetic properties from the stored values in the digital oscilloscope 6. A GPIB (general purpose interface bus) cable 9 interconnects the devices and acts as a built-in communication interface for connecting the computer 8 to other equipment, here shown as oscilloscope 6 and signal generator 1. GPIB handles control instructions and numerical data.

In operation, the present inventive system may amplify the signal waveform at a power amplifier 2 when the output of the signal generator 1 is received therein before being applied to the first coil 4. The H magnetic field can be produced by the amplified current flow in the first coil 4 of a sample material 3.

Since the magnetic flux density B can be produced in the sample material 3 by the magnetic field intensity H, the induced voltage is generated in the second coil 5. The voltage converted through the shunt 7 into the current of the first coil 4 can be input on the first channel of the digital oscilloscope. The induced voltage of the second coil 5 can be input on the second channel of the digital oscilloscope.

The high-frequency waveforms inputted in each channel of the digital oscilloscope 6 are sampled into digital form and then stored in its own memory. Then, the frequency and the maximum value, etc. of the waveform are measured with an analysis of the voltage of each waveform.

Each process step for the measurement is managed and controlled by the computer 8. At first, the computer receives the parameters for the measuring condition from and operator and drives the output of a signal generator 1 the measured valued of the digital oscilloscope 6 are used to obtain the waveforms equivalent to the measuring condition. Finally, the computer controls or determines the output of the signal generator 1 depending on the measured values from the digital oscilloscope 6. This process step is repeated in a step by step manner.

Further, the computer 8 may store the waveforms equivalent to each H and B magnetic field produced by the determined signal output of the signal generator 1 and received by the digital oscilloscope 6. The computer reads the stored waveform from a built-in memory and there obtains the measured value, the H and B curves and the high-frequency hysteresis curve through the numerical calculation such as an integration. For example, as is well known in the art, integration of the magnetic flux density provides a value for core-loss.

A series of control commands and the flow of the numerical data are achieved through the GPIB cables 9 connecting the signal generator and the digital oscilloscope to the computer.

In the present inventive system, it computes the output waveform from a signal input within about 1–2 seconds. The required time to calculate the measured value and the magnetic hysteresis curve may take about 30 seconds.

Most important to the system is to decrease the time taken to complete the recording of the waveform after a signal is applied because heat generation may occur in a short period in the high frequency system.

A measuring frequency range is decided by the consideration of the frequency range of the signal generator 1 and of the cut-off frequency of the power amplifier 2, as well as consideration of the sampling frequency of the digital oscilloscope, which usually rang about 10 Hz to 20 MHz. Since a signal generator has the functions to selectively output a sine-wave, a triangular-wave, a square-wave and so forth, the measuring range of a core-loss can be widened through application of various input waveforms.

Further, as the equipment used in the present invention such as the signal generator, the power amplifier and the digital oscilloscope are for general purpose use, it is very easy to construct, modify and update them. Also, GPIB (general purpose interface bus) is a standard communication protocol, thereby software accompanying the hardware modification and compatibility of the added devices to the existing devices operates extremely well. Thus, the system has a high compatibility of data between devices and an easy process of use and updating.

Generally, in view of observing the result of a B-H curve measurement, the curve is not symmetrical in the origin and a material having a high permeability has more nonsymmetrical curve particularly. This is due to the decreasing effect of the operating magnetic flux density and an increasing effect of the existing current, and thus an error from the core-loss value can be reduced.

So in the present system, symmetrical characteristics of the H signal can be investigated to correct the above error through operation of software design in the computer. It is necessary to have a function which adjusts the symmetrical B-H curve by programming a DC-offset into the signal generator output based on the data from the oscilloscope 6. Thus, a more precise measuring value can be obtained by performing the modification and calculating the DC-offset in the software of the system.

FIGS. 2 through 5 respectively show an illustration of the high frequency magnetic properties measured according to the present invention because they are related to the measuring system of the high-frequency magnetic properties according to the present invention. Only the title of each component is described immediately below in relation to FIGS. 2–5 omitting the detailed explanation of its effect.

Figure 2:
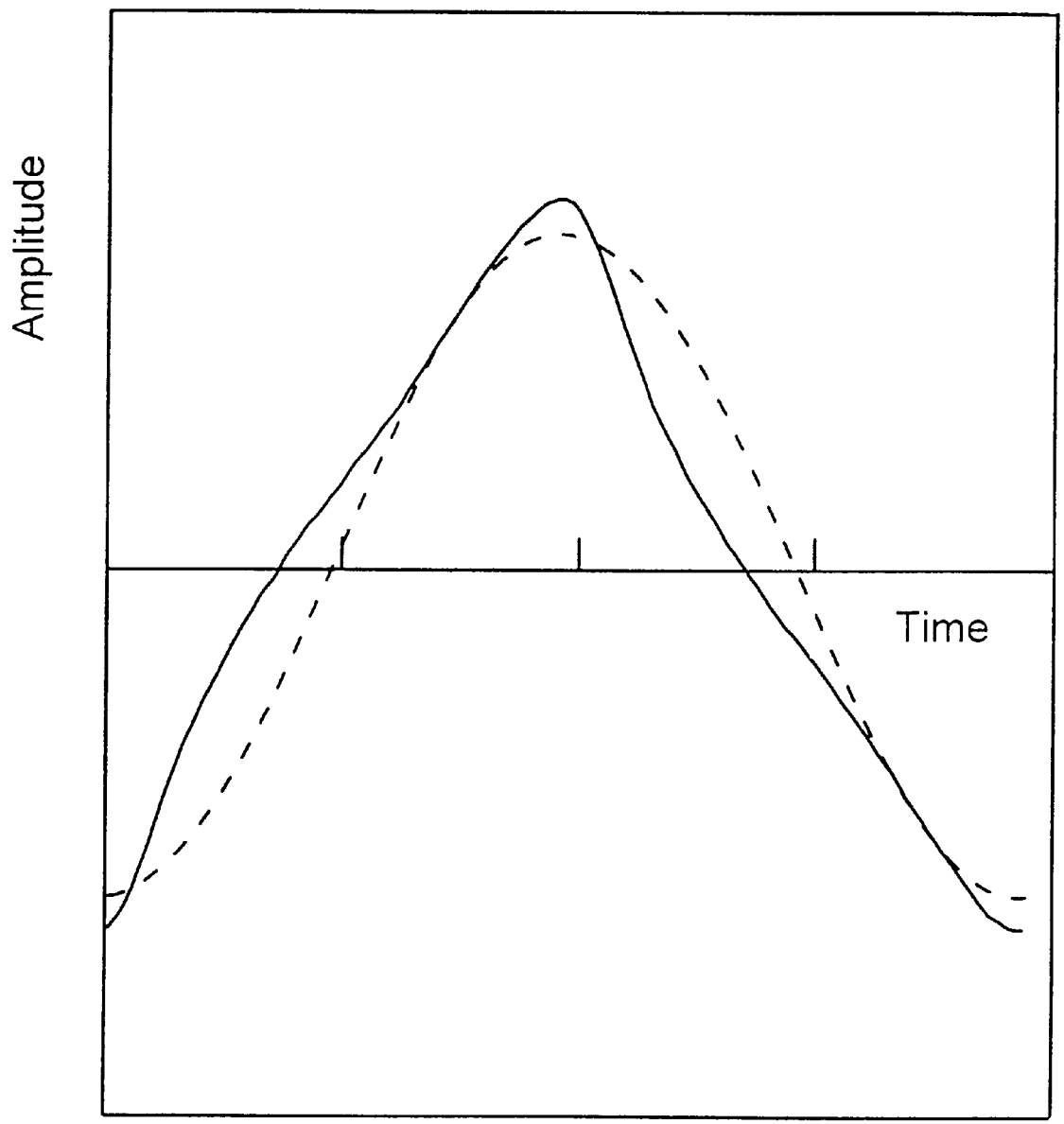
FIG. 2 is a waveform of the B-H magnetic field samples from a digital oscilloscope.

FIG. 2 shows a waveform of a B-H magnetic field which has performed a sampling by the digital oscilloscope, thus having a cycle consisting of 256 data points.

Figure 3:
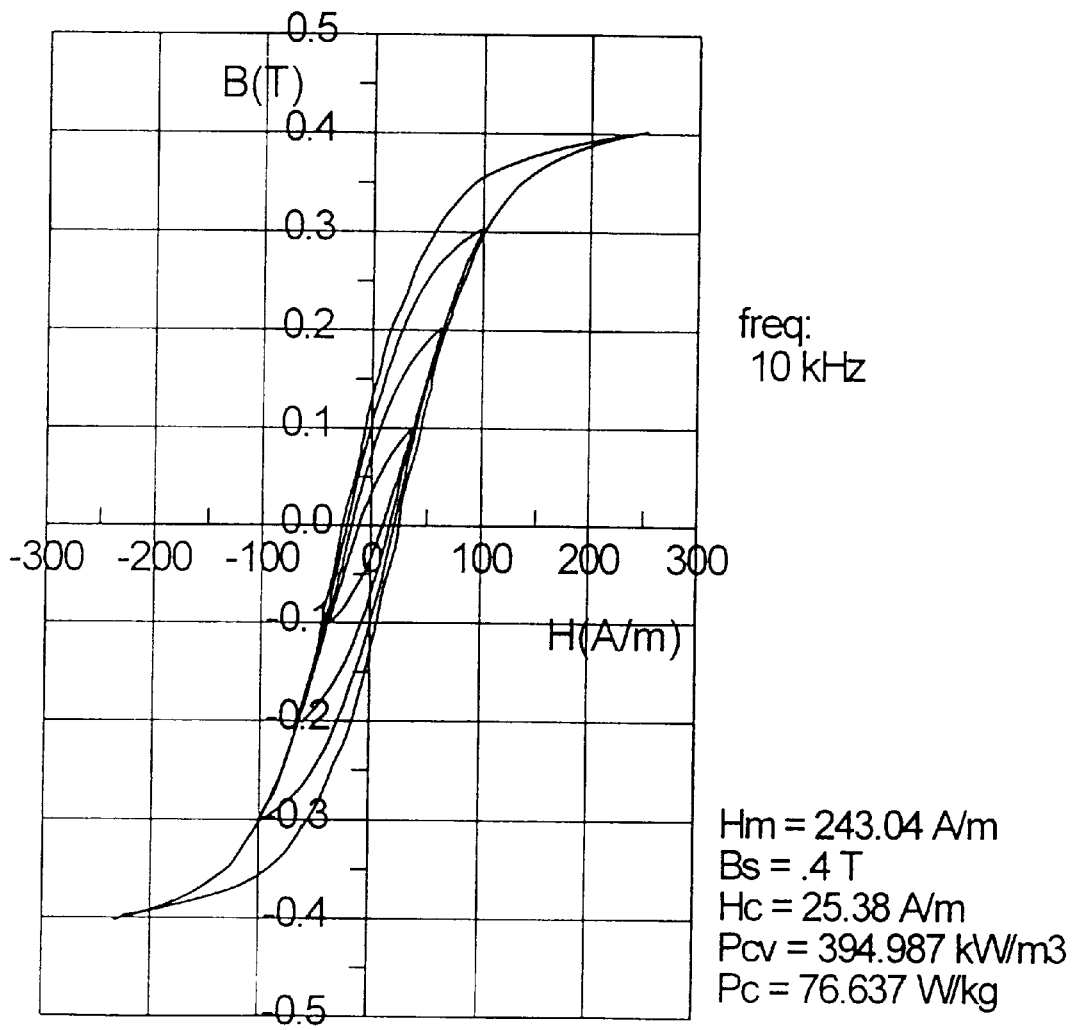
FIG. 3 is a magnetic hysteresis curve for a sample of the amorphous ribbon core according to the operating magnetic flux variations at a frequency of 10 KHz.

FIG. 3 shows a magnetic hysteresis curve of the amorphous ribbon type sample by the change of the operating magnetic flux density at a frequency of 10 KHz, which curve measured at 0.1 T, 0.2 T, 0.3 T and 0.4 T respectively.

Figure 4:
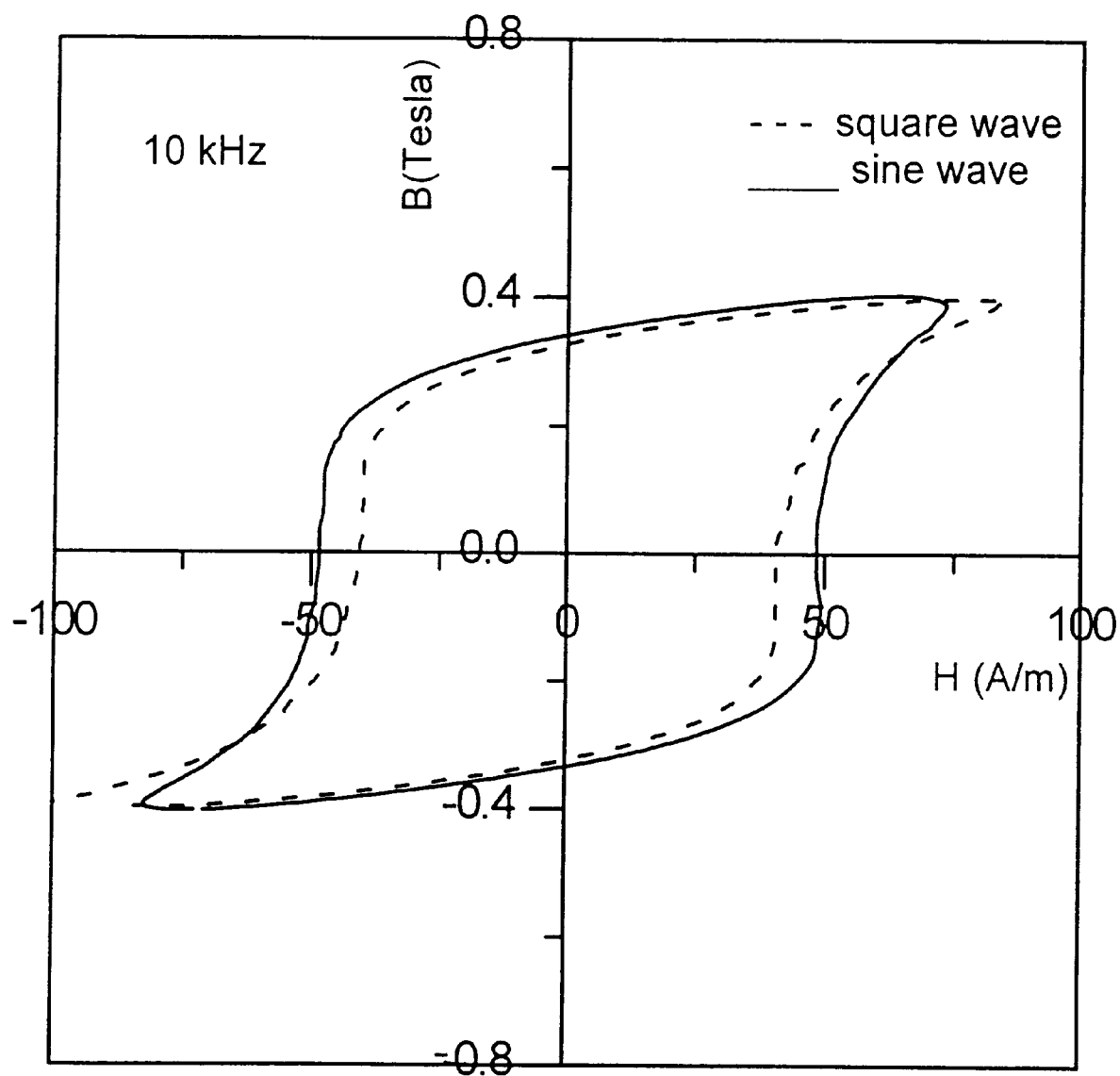
FIG. 4 is a B-H curve for an amorphous ribbon core measured under the condition of an operating magnetic flux 0.4 T and a frequency of 10 KHz.

FIG. 4 shows B-H curves of the amorphous ribbon type core measured under the condition of 0.4 T operation magnetic flux density at a 10 KHz frequency. FIG. 4 shows a variation of the B-H curve when the H-waveform applied as sine wave and a square wave.

Figure 5:
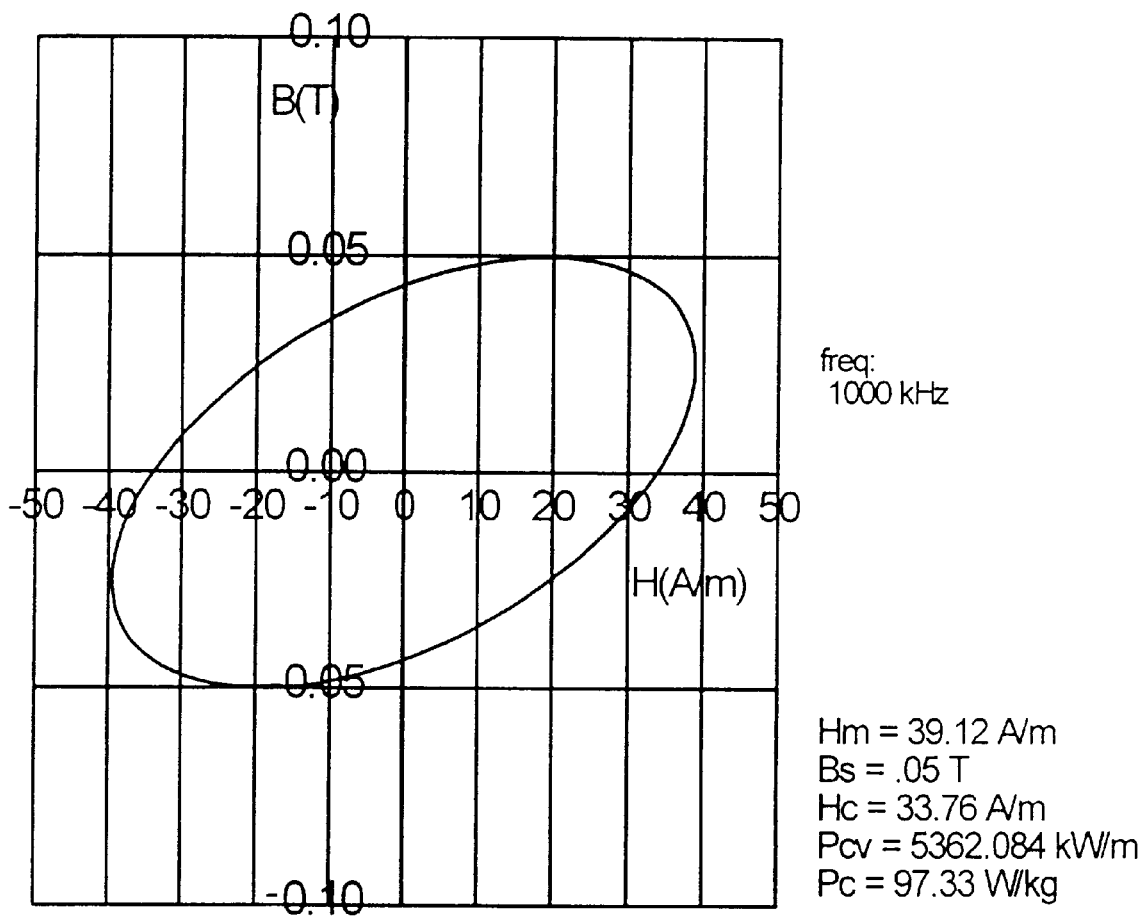
FIG. 5 is a B-H curve for a ferrite measured under the condition of the operating magnetic flux 0.1 T and a frequency of 10 KHz.

FIG. 5 shows a B-H curve of a ferrite ring core measured at 0.1 T operating magnetic flux density and 1 MHz frequency.

Figure 6:
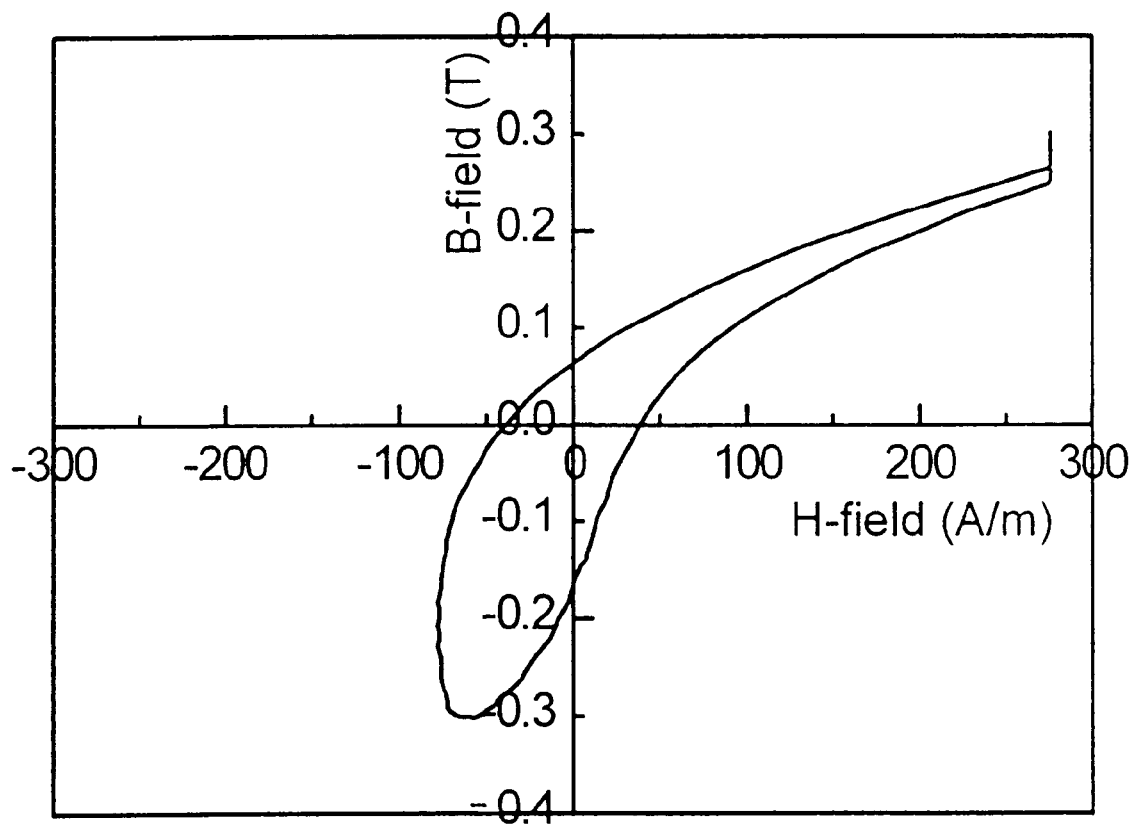
FIG. 6 is an asymmetric B-H curve with the H magnetic field signal biased.

FIG. 6 shows an asymmetrical B-H curve by deviation of the H magnetic field signal, which is indicated an asymmetrical deformation by deviation in a "+" direction of the H magnetic field when it was measured at 0.3 T operating magnetic flux density and 10 KHz frequency.

Figure 7:
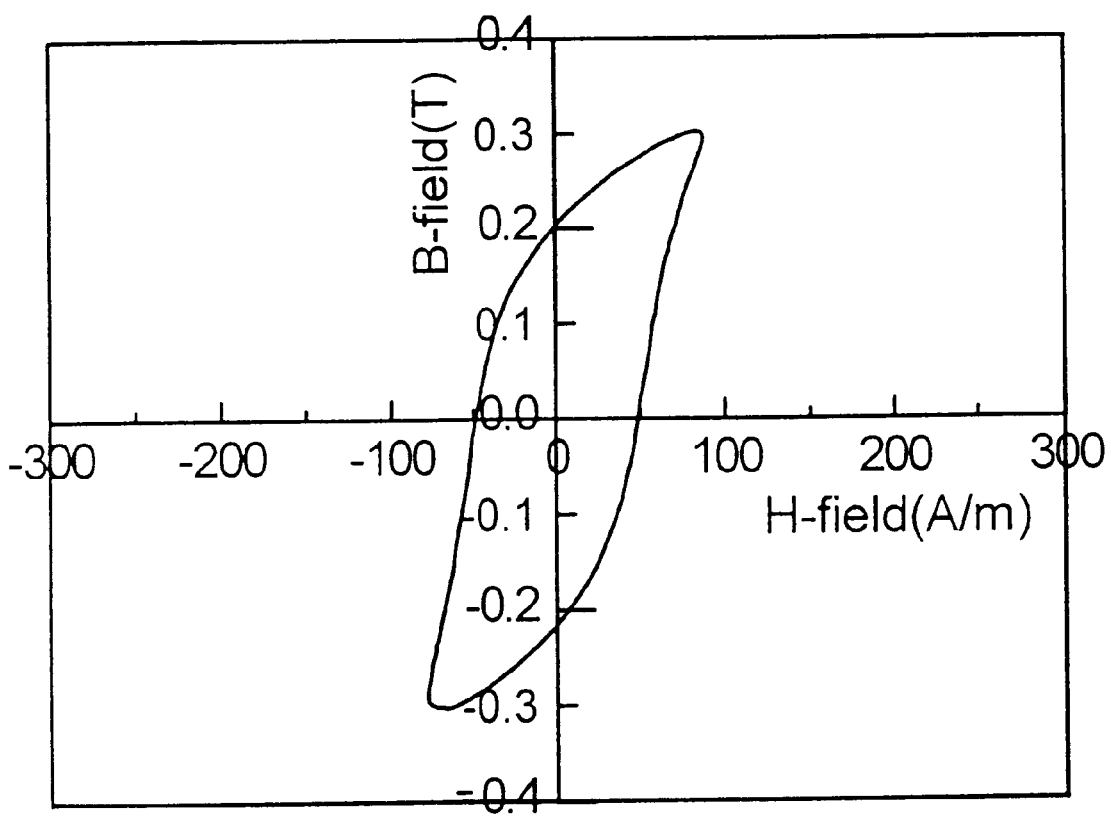
FIG. 7 is a symmetric B-H curve compensated according to an automatic adjusting function.

FIG. 7 shows a symmetrical B-H curve modified by an automatic adjusting function in FIG. 7, the adjusting function produces a symmetrical B-H curve which is a modification of the FIG. 6 curve.

With a combination of the general purpose measuring devices such as a signal generator, an amplifier, a digital oscilloscope and the like, the present invention has a configuration and a function as mentioned above which addresses the drawbacks in the prior art. One effect of the present invention is highly improved performance and reduced economic expense due to constructing a system by the selective adoption of measuring devices having different functions. Another effect is the easily performed modification and upgrading of the measuring system. The effects of modification can be minimized by modifying the software following a hardware modification in the system. The proper software parameters are set following the hardware modification, since the compatibility of the software following a hardware modification, i.e. adding a device, is easily achieved by installing the GPIB interface as the standard communication protocol.

A further effect is obtained in measuring the precise and accurate measuring value and the like. This is achieved by being able to analyze the core-loss as a properly selected waveform for measuring, for example, a square wave, a triangle wave, a saw-tooth wave, a wave formed optionally and the like, as well as by modifying the asymmetrical phenomena of the B-H curve through the modifying function according to the software design.

Thus, the inventive system provides an improved apparatus and method for measuring the effects of a high frequency signal on a sample material. The system operates in a more efficient manner than prior measuring systems by acquiring a digital sample set representing the B-H curve at a higher frequency. The digital sample set is initially stored in the digital oscilloscope and then transferred to a computer for further processing.

Although the particular preferred embodiment of the invention has been disclosed in detail for illustrative purposes, it will be recognized that variations or modifications of the disclosed apparatus, including the rearrangement of parts, lie within the scope of the present invention.

What is claimed is:

1. A high frequency magnetic properties measuring system, comprising:

a signal generator for outputting high frequency signal waveforms in response to input parameters for measuring conditions;

a power amplifier for amplifying the high frequency signal waveforms output from said signal generator;

a shunt connected to the power amplifier and a first coil magnetically coupled to a sample material for converting current of one of the signal waveforms passing through the first coil into a first high-frequency voltage waveform across the shunt;

a digital oscilloscope for receiving the first high-frequency voltage waveform converted from said shunt at a first channel and for receiving at a second channel a second high-frequency voltage waveform induced in a second coil magnetically coupled to the sample material, and spaced from the first coil, by the current passing through the first coil, at respective channels, the digital oscilloscope digitally sampling the received first and second high frequency voltage waveforms at the respective first and second channels, and storing in a memory and analyzing the first high-frequency voltage waveform and the second induced high-frequency voltage waveform to measure and output frequency and maximum values which represent magnetic field intensity signals H and magnetic flux density signals B for the sample material;

a computer for maintaining and controlling said measuring system; and an interface connected to said digital oscilloscope and said computer, wherein said system automatically controls functions and checks for symmetrical properties for plus (+) and minus (−) of the magnetic field intensity signals H corresponding to individual ones of the high frequency signal waveforms output from said signal generator, and said computer is programmed to control a DC-offset of the high frequency signal waveforms of said signal generator based on the first high-frequency voltage waveform and the second high-frequency induced voltage waveform from said oscilloscope to produce a symmetrically formed B-H curve.

2. The high frequency magnetic properties measuring system according to claim 1, wherein individual ones of said second high-frequency induced voltage waveforms correspond to magnetic flux density signals B in order to measure core-loss at a desired working magnetic flux density, and to automatically control said high frequency signal waveforms of said signal generator step by step.

3. The high frequency magnetic properties measuring system according to claim 1, wherein said signal generator selectively outputs a selected high-frequency signal waveform from a group of the high-frequency signal waveforms consisting of sine waves, chopping waves or square waves; and measures core-loss relative to input of said high-frequency signal waveforms and magnetic hysteresis.

4. The high frequency magnetic properties measuring system according to claim 1, wherein said interface comprises a General Purpose Interface Bus (GPIB) which is computer stored communication interface for remote communication between systems connecting the signal generator, the digital oscilloscope and the computer.

5. The high frequency magnetic properties measuring system according to claim 1, wherein the high-frequency signal waveforms include at least one waveform from the group consisting of sine waves, chopping waves or square waves.

6. The high frequency magnetic properties measuring system of claim 1, wherein said computer is capable of sending control commands to said digital oscilloscope.

* * * * *